United States Patent
Inoue et al.

(10) Patent No.: US 11,707,346 B2
(45) Date of Patent: Jul. 25, 2023

(54) DENTAL MILL BLANK AND METHOD FOR PRODUCING SAME

(71) Applicant: KURARAY NORITAKE DENTAL INC., Kurashiki (JP)

(72) Inventors: Masashi Inoue, Niigata (JP); Kenji Hatanaka, Ibaraki (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 406 days.

(21) Appl. No.: 16/957,995

(22) PCT Filed: Dec. 26, 2018

(86) PCT No.: PCT/JP2018/047832
§ 371 (c)(1),
(2) Date: Jun. 25, 2020

(87) PCT Pub. No.: WO2019/131756
PCT Pub. Date: Jul. 4, 2019

(65) Prior Publication Data
US 2020/0360120 A1 Nov. 19, 2020

(30) Foreign Application Priority Data
Dec. 26, 2017 (JP) .............................. 2017-250142

(51) Int. Cl.
| | |
|---|---|
| *A61K 6/77* | (2020.01) |
| *A61K 6/887* | (2020.01) |
| *A61C 13/00* | (2006.01) |
| *A61K 6/76* | (2020.01) |
| *B28B 3/00* | (2006.01) |

(52) U.S. Cl.
CPC ............ *A61C 13/0022* (2013.01); *A61K 6/76* (2020.01); *A61K 6/77* (2020.01); *A61K 6/887* (2020.01); *B28B 3/003* (2013.01)

(58) Field of Classification Search
None
See application file for complete search history.

(56) References Cited

U.S. PATENT DOCUMENTS

| | | | | |
|---|---|---|---|---|
| 6,186,790 B1* | 2/2001 | Karmaker | .......... | A61C 13/0022 433/180 |
| 6,599,125 B1* | 7/2003 | Freilich | ............ | A61C 13/0003 433/180 |
| 2001/0036617 A1* | 11/2001 | Karmaker | ................ | A61C 5/30 433/172 |
| 2003/0125189 A1* | 7/2003 | Castro | .................. | C04B 35/634 264/16 |
| 2004/0241614 A1* | 12/2004 | Goldberg | ........... | A61C 13/0003 428/542.8 |
| 2013/0172441 A1* | 7/2013 | Takahata | ............ | A61C 13/0022 523/115 |
| 2015/0182315 A1* | 7/2015 | Okada | ................ | A61C 13/0006 264/16 |
| 2020/0360120 A1* | 11/2020 | Inoue | ...................... | A61K 6/77 |

FOREIGN PATENT DOCUMENTS

| | | |
|---|---|---|
| JP | 2017-14111 A | 1/2017 |
| JP | 2017-109036 A | 6/2017 |
| WO | WO 2012/042911 A1 | 4/2012 |
| WO | WO 2014/021343 A1 | 2/2014 |
| WO | WO 2017/154850 A1 | 9/2017 |
| WO | WO-2017154850 A1 * | 9/2017 ............. A61C 13/00 |

OTHER PUBLICATIONS

International Search Report dated Mar. 26, 2019 in PCT/JP2018/047832 filed on Dec. 26, 2018, 2 pages.

\* cited by examiner

*Primary Examiner* — Peter A Salamon
(74) *Attorney, Agent, or Firm* — Oblon, McClelland, Maier & Neustadt, L.L.P.

(57) ABSTRACT

The present invention provides a dental mill blank that exhibits desirable resistance against wear in opposing teeth. The present invention relates to a dental mill blank comprising:
an inorganic filler containing an inorganic filler (A) and an inorganic filler (B); and
a polymer,
the inorganic filler (A) partly forming an aggregate, and the dental mill blank satisfying the following formulae (I) to (III), $$0.001 \leq a < 0.32 \quad \text{(I)}$$
$$0.3 \leq b \leq 10 \quad \text{(II)}$$
$$5 \leq x \leq 80 \quad \text{(III),}$$

where a is an average primary particle diameter of the inorganic filler (A) in micrometers, b is an average primary particle diameter of the inorganic filler (B) in micrometers, and x is an average particle diameter of the aggregate in micrometers.

Preferably, the dental mill blank comprises an island component containing the aggregate, and a sea component containing the inorganic filler (A) and the inorganic filler (B).

12 Claims, No Drawings

DENTAL MILL BLANK AND METHOD FOR PRODUCING SAME

TECHNICAL FIELD

The present invention relates to a dental mill blank, and a method for producing same. Specifically, the present invention relates to a dental mill blank suitable for use in the fabrication of dental prostheses such as inlays, onlays, veneers, crowns, bridges, abutment teeth, dental posts, dentures, denture bases, and implant parts (fixtures, abutments) produced by machining using, for example, the dental CAD/CAM system, and to a method for producing same.

BACKGROUND ART

Recent years have seen increasing popularity of the CAD/CAM system, a computer-aided technology for designing and manufacture of inlays, crowns, and other dental prostheses using a milling machine for machining. In the CAD/CAM system, a suitably sized block of a shape such as a cuboid, a cylinder, or a disc is introduced and set on a dental milling machine, and milled into a crown- or dentition-shaped restoration. Various types of block materials have been proposed, including, for example, glass-ceramics, zirconia, titanium, acrylic resins, and composite materials containing polymer resin and inorganic filler.

For example, the dental mill blank producing method described in Patent Literature 1 uses a composite material to enable manufacture of dental prostheses that excel in mechanical strength, wear resistance, and surface gloss, and that exhibit desirable resistance against wear in opposing teeth. In this method, an inorganic filler molded body prepared by pressing an inorganic filler is contacted with a polymerizable monomer-containing composition, and the polymerizable monomer is polymerized and cured. It is stated in Patent Literature 1 that the inorganic filler may be a nanoparticle (ultrafine particle filler), and that the nanoparticle may be an aggregate of nanoparticles. It is also stated that an inorganic ultrafine particle, such as the nanoparticle (ultrafine particle filler), can be mixed with inorganic particles having an average particle diameter of 0.2 to 2 μm to produce a hybrid inorganic particle.

CITATION LIST

Patent Literature

Patent Literature 1: WO 2014/021343 A1

SUMMARY OF INVENTION

Technical Problem

Studies by the present inventors have found that traditional dental mill blanks can still cause wear in opposing teeth when a dental prosthesis obtained from the dental mill blank is placed under the repeated stress of biting, and that the amount of wear in opposing teeth often increases particularly when the dental mill blank is modified to improve mechanical strength such as by varying the composition. That is, further improvements are needed for the dental mill blank of Patent Literature 1 in terms of resistance against wear in opposing teeth.

The present invention has been made to find a solution to the foregoing problem of the related art, and it is an object of the present invention to provide a dental mill blank that exhibits desirable resistance against wear in opposing teeth.

Solution to Problem

The present inventors conducted intensive studies to achieve the foregoing object, and found that a dental mill blank that exhibits desirable resistance against wear in opposing teeth can be obtained when an inorganic filler (A) having an average primary particle diameter of 0.001 μm or more and less than 0.3 μm, and an inorganic filler (B) having an average primary particle diameter of 0.3 μm or more and 10 μm or less are used as inorganic fillers for the production of a dental mill blank containing inorganic filler and polymer, and when the inorganic filler (A) is made to only partly form an aggregate such as by being ultrasonically dispersed in the form of a mixture with inorganic filler (B) in the production of the dental mill blank. The present invention was completed after further studies based on this finding.

The present invention includes the following.

[1] A dental mill blank comprising:
an inorganic filler containing an inorganic filler (A) and an inorganic filler (B); and
a polymer,
the inorganic filler (A) partly forming an aggregate, and the dental mill blank satisfying the following formulae (I) to (III), $$0.001 \leq a < 0.3 \quad \text{(I)}$$

$$0.3 \leq b \leq 10 \quad \text{(II)}$$

$$5 \leq x \leq 80 \quad \text{(III)},$$

where a is an average primary particle diameter of the inorganic filler (A) in micrometers, b is an average primary particle diameter of the inorganic filler (B) in micrometers, and x is an average particle diameter of the aggregate in micrometers.

[2] The dental mill blank according to [1], comprising an island component containing the aggregate, and a sea component containing the inorganic filler (A) and the inorganic filler (B).

[3] The dental mill blank according to [2], wherein the island component has an area fraction of 5 to 20% in a cross section observed with a microscope.

[4] The dental mill blank according to [2] or [3], wherein the sea component has a ratio of [total area of inorganic filler (A) and inorganic filler (B)]/[polymer area] of 60/40 to 80/20 as measured in a cross section observed with a microscope.

[5] The dental mill blank according to any one of [2] to [4], wherein the island component has a ratio of [area of inorganic filler (A)]/[polymer area] of 50/50 to 60/40 as measured in a cross section observed with a microscope.

[6] The dental mill blank according to any one of [1] to [5], wherein the content of the inorganic filler is 70 to 95 mass %.

[7] The dental mill blank according to any one of [1] to [6], wherein the content of the polymer is 5 to 30 mass %.

[8] The dental mill blank according to any one of [1] to [7], wherein the dental mill blank has a mass ratio of [content of inorganic filler (A)]/[content of inorganic filler (B)] of 10/90 to 40/60.

[9] The dental mill blank according to any one of to [8], wherein the content of the aggregate is 2 to 15 mass %.

[10] A method for producing the dental mill blank of any one of [1] to [9], comprising pressing an inorganic filler into an inorganic filler molded body and contacting the inorganic filler molded body and a polymerizable monomer-containing composition with each other, and polymerizing and curing the polymerizable monomer.

[11] The method according to [10], wherein the pressing comprises cold isostatic pressing (CIP).

[12] A method for producing the dental mill blank of any one of [1] to [9], comprising mixing an inorganic filler and a polymerizable monomer-containing composition into a paste, and polymerizing and curing the polymerizable monomer.

Advantageous Effects of Invention

The present invention has provided a dental mill blank that exhibits desirable resistance against wear in opposing teeth.

DESCRIPTION OF EMBODIMENTS

The present invention is described below in detail.

A dental mill blank of the present invention comprises: an inorganic filler containing an inorganic filler (A) and an inorganic filler (B); and a polymer. That is, a dental mill blank of the present invention comprises the following three components: an inorganic filler (A), an inorganic filler (B), and a polymer. In the dental mill blank of the present invention, the inorganic filler (A) is partly forming an aggregate. The dental mill blank of the present invention satisfies the following formulae (I) to (III), $$0.001 \leq a < 0.3 \quad (I)$$

$$0.3 \leq b \leq 10 \quad (II)$$

$$5 \leq x \leq 80 \quad (III),$$

where a is an average primary particle diameter of the inorganic filler (A) in micrometers, b is an average primary particle diameter of the inorganic filler (B) in micrometers, and x is an average particle diameter of the aggregate in micrometers.

With the foregoing configuration, the dental mill blank can exhibit desirable resistance against wear in opposing teeth.

A possible explanation for this effect is as follows, though this is not to be construed as limiting the present invention in any ways. With the inorganic filler (A) partly forming an aggregate, the remaining part of inorganic filler (A) is able to more easily form a denser region with inorganic filler (B). That is, the dental mill blank can easily form a sea component—a region (continuous region) observable in a cross section of dental mill blank by microscopy. Because the inorganic filler (A) of a relatively smaller particle size and the inorganic filler (B) of a relatively larger particle size coexist in the sea component region, the inorganic fillers are able to more easily pack themselves in high density as a whole, and the rigidity improves with the increased mechanical force of engagement between inorganic fillers.

On the other hand, the aggregate formed by inorganic filler (A) easily forms an island component—a region (discontinuous region) observable in a cross section of dental mill blank by microscopy. In the island component region, the inorganic fillers tend to have a lower filling rate than in the dense, rigid region of inorganic fillers containing the non-aggregatory portion of inorganic filler (A) and the inorganic filler (B), as a whole. Accordingly, the island component region tends to have a higher polymer content than the rigid region, and, because of the low elasticity and other properties of the polymer, the island component region is more flexible, and can more easily spread stress under an applied load.

That is, a dental mill blank of the present invention can have a more rigid region where the inorganic fillers are held together with a stronger mechanical force of engagement, and a more flexible region capable of easily spreading stress under an applied load. With these regions, the dental mill blank is able to reduce the amount of wear in opposing teeth under intermittently applied stress, despite having desirable mechanical strength itself. This probably explains the desirable resistance against wear in opposing teeth.

Inorganic Filler

The inorganic filler may be known inorganic particles used as fillers for dental curable compositions, preferably known inorganic particles used as fillers for dental composite resins. Examples of such inorganic particles include various types of glasses (for example, glasses containing boron and/or aluminum and various heavy metals in the main component silicon dioxide (e.g., quartz, fused quartz, silica gel) or silicon), alumina, various types of ceramics, diatomaceous earth, kaolin, clay minerals (e.g., montmorillonite), activated earth, synthetic zeolite, mica, silica, calcium fluoride, ytterbium fluoride, calcium phosphate, barium sulfate, zirconium dioxide (zirconia), titanium dioxide (titania), and hydroxyapatite. The inorganic filler also may be organic-inorganic composite particles (organic-inorganic composite filler) obtained as, for example, pulverized particles of a polymer obtained by polymerizing and curing a polymerizable monomer added to inorganic particles such as above. The inorganic filler may be used alone, or two or more thereof may be used in combination.

Transparency and radiopacity are two important properties of crown restoration materials, and, desirably, crown restoration materials should have the same levels of transparency and radiopacity as those of natural teeth. This level of transparency is achievable by matching the refractive indices of the inorganic filler and the polymer as closely as possible. The desired radiopacity can be imparted by using an inorganic filler (e.g., an oxide) containing a heavy metallic element such as zirconium, barium, titanium, lanthanum, or strontium. Typically, such an inorganic filler containing a heavy metallic element has a high refractive index in a range of 1.5 to 1.6. In the present invention, in the case where, for example, a (meth)acrylic acid ester is used as a polymerizable monomer that forms the polymer, a (meth)acrylic acid ester has a refractive index typically in a range of 1.5 to 1.6, and a small refractive index difference can be achieved even when it is combined with a high-refractive-index inorganic filler having radiopacity. This makes it possible to produce a dental mill blank having improved transparency.

Examples of such high-refractive-index inorganic fillers capable of imparting radiopacity include barium borosilicate glass (for example, E-3000 manufactured by Esstech, and 8235, GM27884, and GM39923 manufactured by Schott), strontium boroaluminosilicate glass (for example, E-4000 manufactured by Esstech, and G018-093 and GM32087 manufactured by Schott), lanthanum glass (for example, GM31684 manufactured by Schott), fluoroaluminosilicate glass (for example, G018-091 and G018-117 manufactured by Schott), zirconia-containing glass (for example, G018-310 and G018-159 manufactured by Schott), strontium-containing glass (for example, G018-163, G018-093, and GM32087 manufactured by Schott), zinc oxide-containing glass (for example, G018-161 manufactured by Schott), and calcium-containing glass (for example, G018-309 manufactured by Schott).

The shape of the inorganic filler is not particularly limited, and the inorganic filler may have a variety of shapes, including, for example, fragments, plates, scales, fibers (e.g., short fibers, long fibers), styluses, whiskers, and spheres. The inorganic filler may have a form of an aggregate of primary particles of a shape such as above, or may be a combination of different shapes, provided that the requirements of the present invention are satisfied. The inorganic filler may be one that has been processed into a shape such as above by being subjected to some kind of process (for example, pulverization).

In the dental mill blank of the present invention, the inorganic filler contains inorganic filler (A) and inorganic filler (B). The dental mill blank satisfies the following formulae (I) and (II), $$0.001 \leq a < 0.3 \quad (I)$$

$$0.3 \leq b \leq 10 \quad (II),$$

where a is the average primary particle diameter of inorganic filler (A) in micrometers, and b is the average primary particle diameter of inorganic filler (B) in micrometers.

The inorganic filler (A) has an average primary particle diameter (a) in a range of 0.001 μm or more and less than 0.3 μm. With the inorganic filler (A) having an average primary particle diameter in this range, the dental mill blank can exhibit desirable resistance against wear in opposing teeth. In view of this, the average primary particle diameter (a) of inorganic filler (A) is preferably 0.002 μm or more, more preferably 0.01 μm or more, even more preferably 0.1 μm or more, and is preferably 0.25 μm or less, more preferably 0.2 μm or less, even more preferably 0.18 μm or less. An overly small average primary particle diameter (a) tends to decrease the mechanical strength of the dental mill blank. An overly large average primary particle diameter (a) may cause difficulty in aggregate formation.

The inorganic filler (B) has an average primary particle diameter (b) in a range of 0.3 μm or more and 10 μm or less. With the inorganic filler (B) having an average primary particle diameter in this range, the dental mill blank can have desirable mechanical strength. In view of this, the average primary particle diameter (b) of inorganic filler (B) is preferably 0.4 μm or more, and may be 0.7 μm or more, 1 μm or more, or 1.5 μm or more, and is preferably 5 μm or less, and may be 4 μm or less, 3 μm or less, or 2.5 μm or less. An overly small average primary particle diameter (b) tends to decrease the mechanical strength of the dental mill blank. An overly large average primary particle diameter (b) may result in the dental mill blank producing a dental prosthesis of poor aesthetic quality.

The average primary particle diameter of the inorganic filler (including inorganic filler (A) and inorganic filler (B)) can be determined by electron microscopy. Specifically, for example, the average primary particle diameter can be determined by taking a micrograph of particles with a scanning electron microscope (SEM; for example, SU3500 manufactured by HITACHI HIGH-TECHNOLOGIES CORPORATION), and measuring the diameter of particles (at least 200 particles) observed in a unit field of the SEM image, using image-analyzing particle-size-distribution measurement software (e.g., Macview manufactured by Mountech Co., Ltd.). Here, the diameter of a particle is determined as the diameter of a corresponding circle having the same area, and the average primary particle diameter is calculated from the number of particles and the particle diameter.

The fraction (b/a) of the average primary particle diameter (b) of inorganic filler (B) to the average primary particle diameter (a) of inorganic filler (A) is preferably 3 or more. In this way, a dental mill blank having more desirable mechanical strength can be obtained. In view of this, the fraction b/a is more preferably 5 or more, even more preferably 7 or more. The upper limit of b/a is not particularly limited, and may be, for example, 70 or less, 40 or less, 25 or less, or 15 or less.

In the dental mill blank, the mass ratio of [content of inorganic filler (A)]/[content of inorganic filler (B)] is preferably 10/90 to 40/60. In this way, the effects of the present invention become more prominent. The mass ratio of [content of inorganic filler (A)]/[content of inorganic filler (B)] is more preferably 13/87 or more, even more preferably 15/85 or more, and is more preferably 38/62 or less, even more preferably 35/65 or less.

A dental mill blank of the present invention may comprise an inorganic filler other than the inorganic fillers (A) and (B). For advantages such as enhancing the effects of the present invention, the combined fraction of inorganic fillers (A) and (B) in all inorganic fillers contained in a dental mill blank of the present invention is preferably 50 mass % or more, more preferably 80 mass % or more, even more preferably 90 mass % or more, and may be 95 mass % or more, 98 mass % or more, or 100 mass %.

Aggregate

In the dental mill blank of the present invention, the inorganic filler (A) is partly forming an aggregate. The aggregate has an average particle diameter (x) in a range of 5 μm to 80 μm By containing an aggregate having an average particle diameter in this range, the dental mill blank can exhibit desirable resistance against wear in opposing teeth. In view of this, the average particle diameter (x) of aggregates is preferably 10 μm or more, more preferably 20 μm or more, and is preferably 70 μm or less, more preferably 60 μm or less. An overly small average particle diameter (x) tends to result in producing a dental mill blank that is more abrasive to opposing teeth. An overly large average particle diameter (x) may result in producing a dental mill blank and, in turn, a dental prosthesis that is more abrasive to opposing teeth and having reduced mechanical strength.

The average particle diameter of aggregates can be determined by electron microscopy. Specifically, for example, the average particle diameter can be determined by taking a micrograph of a cross section of the dental mill blank with a scanning electron microscope (SEM; for example, SU3500 manufactured by HITACHI HIGH-TECHNOLOGIES CORPORATION), and measuring the particle diameter of aggregates (at least 200 aggregates) observed in a unit field of the SEM image, using image-analyzing particle-size-distribution measurement software (e.g., Macview manufactured by Mountech Co., Ltd.). Here, the particle diameter of an aggregate is determined as the diameter of a corresponding circle having the same area, and the average particle diameter is calculated from the number of aggregates and the particle diameter. More specifically, the average particle diameter of aggregates can be determined by the method described in the EXAMPLES section below.

In a dental mill blank of the present invention, it is preferable that the aggregate be forming an island component containing the aggregate. In this case, it is preferable that the region other than the island component be forming a sea component containing inorganic filler (A) and inorganic filler (B). The dental mill blank of the present invention can exhibit more desirable resistance against wear in opposing teeth when it contains the aggregate-containing island component, and the sea component containing inorganic filler (A) and inorganic filler (B). The island component is observable as a discontinuous region by microscopy of a cross section of the dental mill blank. The sea component is observable as a continuous region by microscopy of a cross section of the dental mill blank. The polymer contained in the dental mill blank of the present invention may be contained only in the island component or only in the sea component. However, for advantages such as enhancing the effects of the present invention, it is preferable that the polymer be contained in both the island component and the sea component.

When the dental mill blank of the present invention has an island-in-sea structure such as above, it is preferable that the area fraction of the island component observed in a cross section of the dental mill blank under a microscope fall in a range of 5 to 20%. In this way, the dental mill blank can have improved mechanical strength and exhibit more desirable resistance against wear in opposing teeth. In view of this, the area percentage of island component is more preferably 7% or more, even more preferably 10% or more, and is more preferably 18% or less, even more preferably 15% or less.

The area fraction of the island component can be determined by using image-analyzing particle-size-distribution measurement software (e.g., Macview manufactured by Mountech Co., Ltd.). For example, the area fraction of the island component can be determined by measuring the area of all observable aggregates (the total area of aggregates) at arbitrary spots in a SEM image taken by electron microscopy at 100 to 500 times magnification, and dividing the measured value by the whole area. More specifically, the area fraction of the island component can be determined using the method described in the EXAMPLES section below.

When the dental mill blank of the present invention has an island-in-sea structure such as above, it is preferable that the ratio [total area of inorganic filler (A) and inorganic filler (B)]/[polymer area] in the sea component observed in a cross section of the dental mill blank under a microscope fall in a range of 60/40 to 80/20. In this way, the dental mill blank can have improved mechanical strength. In view of this, the ratio [total area of inorganic filler (A) and inorganic filler (B)]/[polymer area] in the sea component is more preferably 61/39 or more, even more preferably 62/38 or more, and is more preferably 78/22 or less, even more preferably 77/23 or less.

The ratio [total area of inorganic filler (A) and inorganic filler (B)]/[polymer area] in the sea component can be determined using image-analyzing particle-size-distribution measurement software (e.g., Macview manufactured by Mountech Co., Ltd.). For example, the ratio can be determined by finding the total area of all inorganic fillers (A), the total area of all inorganic fillers (B), and the total area of all polymers in the sea component observable at arbitrary spots in a SEM image taken by electron microscopy at 100 to 500 times magnification, and dividing the sum of the total areas of inorganic fillers (A) and (B) by the total area of polymers. More specifically, the ratio can be determined using the method described in the EXAMPLES section below.

When the dental mill blank of the present invention has an island-in-sea structure such as above, it is preferable that the ratio [area of inorganic filler (A)]/[polymer area] in the island component observed in a cross section of the dental mill blank under a microscope fall in a range of 50/50 to 60/40. In this way, the dental mill blank can exhibit more desirable resistance against wear in opposing teeth. In view of this, the ratio [area of inorganic filler (A)]/[polymer area] in the island component is more preferably 51/49 or more, and is more preferably 57/43 or less, even more preferably 54/46 or less.

The ratio [area of inorganic filler (A)]/[polymer area] in the island component can be determined using image-analyzing particle-size-distribution measurement software (e.g., Macview manufactured by Mountech Co., Ltd.). For example, the ratio can be determined by finding the total area of all inorganic fillers (A) and the total area of all polymers in the island component observable at arbitrary spots in a SEM image taken by electron microscopy at 100 to 500 times magnification, and dividing the total area of inorganic filler (A) by the total area of polymers. More specifically, the ratio can be determined using the method described in the EXAMPLES section below.

For advantages such as enhancing the effects of the present invention, the aggregate content in a dental mill blank of the present invention is preferably 2 mass % or more, more preferably 4 mass % or more, even more preferably 5 mass % or more, and is preferably 15 mass % or less, more preferably 13 mass % or less, even more preferably 12 mass % or less.

Surface Treatment

The inorganic filler is preferably one subjected to a surface treatment in advance. The dental mill blank produced can have improved mechanical strength by using an inorganic filler that has been subjected to a surface treatment. Another advantage is that the affinity between a polymerizable monomer-containing composition (described later) and the surface of the inorganic filler improves, and the polymerizable monomer-containing composition is able to more easily penetrate into spaces between inorganic filler particles such as when the polymerizable monomer-containing composition is contacted with an inorganic filler molded body prepared by pressing the inorganic filler.

Only one of the inorganic filler (A) and the inorganic filler (B) may be subjected to a surface treatment, or both of the inorganic filler (A) and the inorganic filler (B) may be subjected to a surface treatment. In the case of the latter, the inorganic filler (A) and the inorganic filler (B) may prepared by being individually subjected to a surface treatment, or by performing a surface treatment for a mixture of inorganic filler (A) and inorganic filler (B). A surface treatment may be carried out for individual primary particles of inorganic filler (A) forming the aggregate, or for the aggregate itself.

The surface treatment agent used for surface treatment may be a known surface treatment agent. Examples of such surface treatment agents include: organometallic compounds such as organosilicon compounds, organotitanium compounds, organozirconium compounds, and organoaluminum compounds; and organic compounds having at least one acidic group such as a phosphoric acid group, a pyrophosphoric acid group, a thiophosphoric acid group, a phosphonic acid group, a sulfonic acid group, or a carboxylic acid group (acidic group-containing organic compounds). The surface treatment agent may be used alone, or two or more thereof may be used in combination. When using two or more surface treatment agents in combination, the surface treatment layer may be a layer formed by a mixture of two or more surface treatment agents, or may be a laminate structure of multiple surface treatment layers. The surface treatment method is not particularly limited, and a known method may be used.

Examples of the organosilicon compounds include compounds represented by, for example, $R^1{}_n SiX_{4-n}$ (wherein $R^1$ is a substituted or unsubstituted hydrocarbon group having 1 to 12 carbon atoms, X represents an alkoxy group having 1 to 4 carbon atoms, an acetoxy group, a hydroxyl group, a halogen atom, or a hydrogen atom, and n is an integer of 0 to 3, in which $R^1$ may be the same or different when a plurality of $R^1$ exists, and X may be the same or different when a plurality of X exists).

Specific examples of the organosilicon compounds include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyl diethoxysilane, N-(β-aminoethyl)γ-aminopropylmethyldimethoxysilane, N-(β-aminoethyl)γ-aminopropyltrimethoxysilane, aminoethyl)γ-aminopropyltriethoxysilane, γ-aminopropyltrimethoxysilane, γ-aminopropyltriethoxysilane, N-phenyl-γ-aminopropyltrimethoxysilane, ymercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloyloxyalkyltrimethoxysilane (having 3 to 12 carbon atoms between the (meth)acryloyloxy group and the silicon atom; e.g., γ-methacryloyloxypropyltrimethoxysilane), and ω-(meth)acryloyloxyalkyltriethoxysilane (having 3 to 12 carbon atoms between the (meth)acryloyloxy group and the silicon atom; e.g., γ-methacryloyloxypropyltriethoxysilane). As used herein, "(meth)acryloyl" is meant to be inclusive of both "methacryloyl" and "acryloyl".

For advantages such as strengthening the chemical bonding between the inorganic filler and the polymerizable monomer and further improving the mechanical strength of the dental mill blank, the organosilicon compounds are preferably those having a functional group that is copolymerizable with the polymerizable monomer, more preferably ω-(meth)acryloyloxyalkyltrimethoxysilane (having 3 to 12 carbon atoms between the (meth)acryloyloxy group and the silicon atom), ω-(meth)acryloyloxyalkyltriethoxysilane (having 3 to 12 carbon atoms between the (meth) acryloyloxy group and the silicon atom), vinyltrimethoxysilane, vinyltriethoxysilane, vinyltriacetoxysilane, and γ-glycidoxypropyltrimethoxysilane.

Examples of the organotitanium compounds include tetramethyl titanate, tetraisopropyl titanate, tetra-n-butyl titanate, a butyl titanate dimer, and tetra(2-ethylhexyl)titanate.

Examples of the organozirconium compounds include zirconium isopropoxide, zirconium n-butoxide, zirconium acetylacetonate, and zirconium acetate.

Examples of the organoaluminum compounds include aluminum acetylacetonate, and an aluminum-organic acid salt chelate compound.

Examples of the organic compounds having a phosphoric acid group(s) include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, ammonium salts thereof.

Aside from the foregoing organic compounds having an acidic group(s) such as a pyrophosphoric acid group, a thiophosphoric acid group, a phosphonic acid group, a sulfonic acid group, and a carboxylic acid group, the acidic group-containing organic compounds mentioned in, for example, WO 2012/042911 A1 may be used.

The amount of surface treatment agent is not particularly limited, and is preferably, for example, 0.1 to 50 parts by mass relative to 100 parts by mass of the inorganic filler before surface treatment.

Binder

The inorganic filler may be one forming an inorganic filler complex having a binder on its surface. An inorganic filler complex having a binder on its surface can be obtained by mixing the inorganic filler with a binder. By using an inorganic filler complex having a binder on its surface, the inorganic filler (inorganic filler complex) can be pressed with improved formability, and cracking and chipping in the resulting inorganic filler molded body can be reduced. Another advantage is that the affinity between a polymerizable monomer-containing composition (described later) and the surface of the inorganic filler improves such as when contacting the inorganic filler molded body and the polymerizable monomer-containing composition with each other for penetration of the polymerizable monomer-containing composition into spaces between inorganic filler particles, or when mixing the inorganic filler and the polymerizable monomer-containing composition into a paste. This improves the mechanical strength of the dental mill blank obtained.

Only one of the inorganic filler (A) and the inorganic filler (B) may be forming an inorganic filler complex having a binder on its surface. It is, however, preferable that an inorganic filler complex having a binder on its surface be formed by both inorganic filler (A) and inorganic filler (B). The inorganic filler complex having a binder on its surface may be formed by individual primary particles of inorganic filler (A) forming the aggregate, or by the aggregate itself.

The binder is not limited to a particular kind of binder, and may be, for example, a polymerizable monomer (e.g., a radical polymerizable monomer, a cationic polymerizable monomer), a polymer of a polymerizable monomer, a wax, or a plasticizer. The binder may be used alone, or two or more thereof may be used in combination. For advantages such as further improving the mechanical strength of a dental mill blank produced by thermal polymerization and curing of a polymerizable monomer such as by a method that includes contacting the inorganic filler molded body and the polymerizable monomer-containing composition with each other and polymerizing and curing the polymerizable monomer, or a method that includes mixing the inorganic filler and the polymerizable monomer-containing composition into a paste, and polymerizing and curing the polymerizable monomer, it is preferable that the binder contained in the inorganic filler complex before polymerization and curing (for example, at the time of pressing, or a state of being a paste) be at least one selected from the group consisting of a polymerizable monomer, a wax, and a plasticizer, more preferably at least one selected from the group consisting of a polymerizable monomer and a plasticizer, even more preferably a polymerizable monomer. The binder contained in the inorganic filler complex after polymerization and curing (for example, the binder contained in the dental mill blank produced) is preferably at least one selected from the group consisting of a polymer of a polymerizable monomer, a wax, and a plasticizer, more preferably at least one selected from the group consisting of a polymer of a polymerizable monomer, and a plasticizer, even more preferably a polymer of a polymerizable monomer.

Specific examples of the polymerizable monomer used as the binder include polymerizable monomers mentioned below as polymerizable monomers that form the polymer contained in the dental mill blank. Preferred are radical polymerizable monomers. The polymerizable monomer used as the binder is preferably at least one of polymerizable monomers that form the polymer contained in the product dental mill blank (typically, a polymerizable monomer contained in the polymerizable monomer-containing composition described below). Likewise, specific examples of the polymer used as the binder include polymers obtained through polymerization of polymerizable monomers mentioned below as polymerizable monomers that form the polymer contained in the dental mill blank. Preferred are polymers obtained through polymerization of radical polymerizable monomers. The polymer used as the binder is preferably a polymer obtained through polymerization of at least one of polymerizable monomers that form the polymer contained in the product dental mill blank (typically, a polymerizable monomer contained in the polymerizable monomer-containing composition described below).

The polymerizable monomer is preferably a bifunctional (meth)acrylic acid ester, more preferably 2,2-bis[4-[3-acryloyloxy-2-hydroxypropoxy]phenyl]propane, 2,2-bis[4-[3-methacryloyloxy-2-hydroxypropoxy]phenyl]propane (commonly known as Bis-GMA), 2,2-bis[4-(meth)acryloyloxyethoxyphenyl]propane, 2,2-bis[4-(meth)acryloyloxypolyethoxyphenyl]propane, or [2,2,4-trimethylhexamethylenebis(2-carbamoyloxyethyl)]dimethacrylate (commonly known as UDMA), though it depends on factors such as the type of the polymerizable monomer that forms the polymer contained in the dental mill blank.

Examples of the wax include paraffin wax, polyethylene wax, polyolefin wax, and liquid paraffin wax.

Examples of the plasticizer include phthalic acid esters such as dimethyl phthalate, diethyl phthalate, dibutyl phthalate, di(2-ethylhexyl) phthalate, di-n-octyl phthalate, diisononyl phthalate, dinonyl phthalate, diisodecyl phthalate, and butyl benzyl phthalate; adipic acid esters such as dioctyl adipate, diisononyl adipate, di-n-hexyl adipate, and di-n-decyl adipate; and polyethylene glycol (PEG).

The amount of binder is not particularly limited. However, the amount of binder, in terms of a content in the inorganic filler complex, is preferably 0.1 mass % or more, more preferably 0.3 mass % or more, even more preferably 0.5 mass % or more, and is preferably 10 mass % or less, more preferably 5 mass % or less, even more preferably 3 mass % or less. With these lower limits of binder content, the binder is able to more effectively exhibit its effect. With the foregoing upper limits of binder content, the fluidity improves, and a dental mill blank having excellent mechanical strength with reduced cracks and chipping can be produced with improved yield.

The inorganic filler content in a dental mill blank of the present invention is preferably 70 mass % or more, more preferably 75 mass % or more, even more preferably 80 mass % or more, and is preferably 95 mass % or less, more preferably 93 mass % or less, even more preferably 90 mass % or less. In this way, the dental mill blank can have improved mechanical strength and more desirable aesthetic quality.

The inorganic filler content can be determined by ashing the dental mill blank. Ashing of a dental mill blank containing inorganic filler and polymer typically burns the organic components, including the polymer. The inorganic filler content in a dental mill blank can thus be determined by dividing the mass of the product after ashing by the mass before ashing. The ashing may be, for example, a process that heats the dental mill blank in a crucible at 575° C. for a predetermined time (for example, 2 hours), using an electric furnace or the like. When the inorganic filler is one subjected to a surface treatment, or when the inorganic filler complex having a binder on its surface is used, ashing performed under the foregoing conditions typically burns the surface treatment agent or binder-derived components as organic components.

Polymer

The constituent polymer of a dental mill blank of the present invention is not particularly limited, and may be a polymer of a polymerizable monomer, preferably a polymer resulting from polymerization and curing of a polymerizable monomer contained in the polymerizable monomer-containing composition.

Polymerizable Monomer

The polymerizable monomer that forms the polymer (the polymerizable monomer that forms the structural unit contained in the polymer) may be a known polymerizable monomer used for applications such as dental composite resins. Typically, preferred for use are radical polymerizable monomers. Specific examples of the radical polymerizable monomers include esters of carboxylic acids such as α-cyanoacrylic acid, (meth)acrylic acid, α-halogenated acrylic acid, crotonic acid, cinnamic acid, sorbic acid, maleic acid, and itaconic acid; (meth)acrylamide; derivatives of (meth)acrylamide; vinyl esters; vinyl ethers; mono-N-vinyl derivatives; and styrene derivatives. The radical polymerizable monomers are preferably carboxylic acid esters, and derivatives of (meth)acrylamide, more preferably (meth)acrylic acid esters, and derivatives of (meth)acrylamide, even more preferably (meth)acrylic acid esters. As used herein, "(meth)acryl" is meant to be inclusive of both methacryl and acryl. Examples of the (meth)acrylic acid esters, and derivatives of (meth)acrylamide are as follows.

(i) Monofunctional (Meth)Acrylic Acid Esters, and Derivatives of (Meth)Acrylamide Examples include methyl(meth)acrylate, isobutyl(meth)acrylate, benzyl(meth)acrylate, lauryl(meth)acrylate, 2-(N,N-dimethylamino)ethyl(meth)acrylate, 2,3-dibromopropyl(meth)acrylate, 2-hydroxyethyl(meth)acrylate, 6-hydroxyhexyl(meth)acrylate, 10-hydroxydecyl(meth)acrylate, propylene glycol mono(meth)acrylate, glycerin mono(meth)acrylate, erythritol mono(meth)acrylate, N-methylol(meth)acrylamide, N-hydroxyethyl(meth)acrylamide, N,N-bis(hydroxyethyl)(meth)acrylamide, (meth)acryloyloxy dodecylpyridinium bromide, (meth)acryloyloxy dodecylpyridinium chloride, (meth)acryloyloxy hexadecylpyridinium chloride, (meth)acryloyloxy decylammonium chloride, and 10-mercaptodecyl(meth)acrylate.

(ii) Bifunctional (Meth)Acrylic Acid Esters

Examples include ethylene glycol di(meth)acrylate, triethylene glycol di(meth)acrylate, propylene glycol di(meth)acrylate, neopentyl glycol di(meth)acrylate, 1,6-hexanediol di(meth)acrylate, 1,10-decanediol di(meth)acrylate, 2,2-bis[4-[3-acryloyloxy-2-hydroxypropoxy]phenyl]propane, 2,2-bis[4-[3-methacryloyloxy-2-hydroxypropoxy]phenyl]propane (Bis-GMA), 2,2-bis[4-(meth)acryloyloxyethoxyphenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, [2,2,4-trimethylhexamethylenebis(2-carbamoyloxyethyl)]dimethacrylate (UDMA), and 2,2,3,3,4,4-hexafluoro-1,5-pentyl di(meth)acrylate.

(iii) Tri- and Higher-Functional (Meth)Acrylic Acid Esters

Examples include trimethylolpropane tri(meth)acrylate, trimethylolethane tri(meth)acrylate, tetramethylolmethane tri(meth)acrylate, pentaerythritoltetra(meth)acrylate, dipentaerythritol hexa(meth)acrylate, N,N'-(2,2,4-trimethylhexamethylene)bis[2-(aminocarboxy)propane-1,3-diol]tetra(met h)acrylate, and 1,7-diacryloyloxy-2,2,6,6-tetra(meth)acryloyloxymethyl-4-oxyheptane.

Aside from the radical polymerizable monomers, cationic polymerizable monomers such as oxirane compounds and oxetane compounds may be used as polymerizable monomers.

The polymerizable monomer may be used alone, or two or more thereof may be used in combination. Preferably, the polymerizable monomer is liquid form. However, the polymerizable monomer is not necessarily required to be liquid form at ordinary temperature, and it is also possible to use a solid polymerizable monomer, or a dissolved mixture with other liquid polymerizable monomers.

The polymerizable monomer has a viscosity (25° C.) of preferably 10 Pa·s or less, more preferably 5 Pa·s or less, even more preferably 2 Pa·s or less. When two or more polymerizable monomers are used as a mixture, or when the polymerizable monomer(s) are used by being diluted with a solvent, it is not required to confine the viscosities of individual polymerizable monomers in these ranges. It is, however, preferable that the viscosity of the polymerizable monomer(s) fall in the foregoing ranges in a ready-to-use form (a mixed or diluted form).

Polymerization Initiator

For ease of polymerization, a polymerization initiator may be used in obtaining a polymer through polymerization of the polymerizable monomer. Particularly, when the polymerizable monomer in the polymerizable monomer-containing composition is polymerized and cured to obtain a polymer, it is preferable that the polymerizable monomer-containing composition additionally contain a polymerization initiator. The polymerization initiator may be selected from polymerization initiators commonly used in industry, preferably from those used in dentistry. For example, the polymerization initiator may be at least one selected from the group consisting of a thermal polymerization initiator, a photopolymerization initiator, and a chemical polymerization initiator.

(i) Thermal Polymerization Initiator

Examples of the thermal polymerization initiator include organic peroxides and azo compounds.

Examples of the organic peroxides include ketone peroxides, hydroperoxides, diacyl peroxides, dialkyl peroxides, peroxy ketals, peroxy esters, and peroxydicarbonates.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxy esters include α-cumyl peroxyneodecanoate, t-butyl peroxyneodecanoate, t-butyl peroxypivalate, 2,2,4-trimethylpentyl peroxy-2-ethyl hexanoate, t-amyl peroxy-2-ethyl hexanoate, t-butyl peroxy-2-ethyl hexanoate, di-t-butyl peroxyisophthalate, di-t-butyl peroxyhexahydroterephthalate, t-butyl peroxy-3,3,5-trimethyl hexanoate, t-butyl peroxyacetate, t-butyl peroxybenzoate, and t-butyl peroxymaleate.

Examples of the peroxydicarbonates include di-3-methoxyperoxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Of these organic peroxides, preferred for an overall balance of safety, storage stability, and radical generating potential are diacyl peroxides, particularly benzoyl peroxide.

Examples of the azo compounds include 2,2'-azobis(isobutyronitrile), 2,2'-azobis(2,4-dimethylvaleronitrile), 4,4'-azobis(4-cyanovaleric acid), 1,1'-azobis(cyclohexane-1-carbonitrile), dimethyl-2,2'-azobis(isobutyrate), and 2,2'-azobis(2-amidinopropane)dihydrochloride.

(ii) Photopolymerization Initiator

Suitable as the photopolymerization initiator are those widely used for curable compositions in dentistry, for example, such as (bis)acylphosphine oxides, α-diketones, and coumarins.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di(2,6-dimethylphenyl)phosphonate, and salts thereof.

Examples of bisacylphosphine oxides in the (bis)acylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6- dimethoxybenzoyl)-2,5-dimethylphenylphosphine oxide, bis(2,4,6-trimethylbenzoyl)phenylphosphine oxide, bis(2,3,6-trimethylbenzoyl)-2,4,4-trimethylpentylphosphine oxide, and salts thereof.

Preferred as the (bis)acylphosphine oxides are sodium salts of 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide.

Examples of the ordiketones include diacetyl, benzyl, camphorquinone, 2,3-pentadione, 2,3-octadione, 9,10-phenanthrenequinone, 4,4'-oxybenzyl, and acenaphthenequinone. Preferred is camphorquinone.

Examples of the coumarins include 3,3'-carbonylbis(7-diethylaminocoumarin), 3-(4-methoxybenzoyl)coumarin, 3-thienyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrrano[6,7,8-ij]quinolizin-11-one, and 10-(2-benzothiazoyl)-2,3,6,7-tetrahydro-1,1,7,7-tetramethyl-1H,5H,11H-[1]benzopyrrano[6,7,8-ij]quinolizin-11-one.

Preferred among these coumarin compounds are 3,3'-carbonylbis(7-diethylaminocoumarin) and 3,3'-carbonylbis(7-dibutylaminocoumarin).

(iii) Chemical Polymerization Initiator Examples of the chemical polymerization initiator include redox polymerization initiators. The preferred redox polymerization initiators are, for example, organic peroxide-amine polymerization initiators; and organic peroxide-amine-sulfinic acid (or a salt thereof) polymerization initiators. When using a redox polymerization initiator, it is preferable to prepare the oxidizing agent and the reducing agent as separate packages, and mix the two immediately before use.

Examples of the oxidizing agent of redox polymerization initiators include organic peroxides. The organic peroxides may be known organic peroxides.

Specifically, the organic peroxides exemplified above in conjunction with the thermal polymerization initiator may be used. For an overall balance of safety, storage stability, and radical generating potential, the organic peroxides are preferably diacyl peroxides, particularly benzoyl peroxide.

The reducing agent of redox polymerization initiators is typically a tertiary aromatic amine having no electron withdrawing group on the aromatic ring.

Examples of tertiary aromatic amines having no electron withdrawing group on the aromatic ring include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, and N,N-bis(2-hydroxyethyl)-3,5-di-t-butylaniline.

The polymerization initiator may be used alone, or two or more thereof may be used in combination. For example, the polymerization initiator may be a combination of a thermal polymerization initiator and a photopolymerization initiator. In this case, it is preferable to combine a diacyl peroxide and a (bis)acylphosphine oxide.

The amount of polymerization initiator is not particularly limited. However, in view of considerations such as ease of polymerization, the polymerization initiator is preferably 0.001 parts by mass or more, more preferably 0.05 parts by mass or more, even more preferably 0.1 parts by mass or more relative to 100 parts by mass of the polymerizable monomer. With these lower limits of polymerization initiator content, polymerization sufficiently takes place even when the polymerization initiator itself is not highly polymerizable, and the resulting dental mill blank, and, in turn, the dental prosthesis produced therefrom, can have improved strength. The polymerization initiator is preferably 30 parts by mass or less, more preferably 20 parts by mass or less relative to 100 parts by mass of the polymerizable monomer. With the foregoing upper limits of polymerization initiator content, it is possible to inhibit precipitation of polymerization initiator.

Polymerization Accelerator

When using a polymerization initiator, the polymerization initiator may be used with a polymerization accelerator. Particularly, when the polymerizable monomer in the polymerizable monomer-containing composition is polymerized and cured to obtain a polymer, the polymerizable monomer-containing composition may also contain a polymerization accelerator, in addition to the polymerization initiator.

By using a polymerization accelerator with the polymerization initiator, polymerization can take place more quickly and more efficiently. The polymerization accelerator may be selected from polymerization accelerators commonly used in industry, preferably from those used in dentistry. The polymerization accelerator may be used alone, or two or more thereof may be used in combination.

Examples of polymerization accelerators preferred for use with the photopolymerization initiator include tertiary amines, aldehydes, thiols, and sulfinic acid and salts thereof.

Examples of the tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t- butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, n-butoxyethyl 4-(N,N-dimethylamino)benzoate, (2-methacryloyloxy)ethyl 4-(N,N-dimethylamino)benzoate, ethyl 4-(N,N-dimethylamino)benzoate, butyl 4-(N,N-dimethylamino)benzoate, N-methyldiethanolamine, 4-(N,N-dimethylamino)benzophenone, trimethylamine, triethylamine, N-methyldiethanolamine, N-ethyldiethanolamine, N-n-butyldiethanolamine, N-lauryldiethanolamine, triethanolamine, 2-(dimethylamino)ethylmethacrylate, N-methyldiethanolamine dimethacrylate, N-ethyldiethanolamine dimethacrylate, triethanolamine monomethacrylate, triethanolamine dimethacrylate, and triethanolaminetrimethacrylate.

Examples of the aldehydes include dimethylaminobenzaldehyde and terephthalaldehyde.

Examples of the thiols include 2-mercaptobenzooxazole, decanethiol, 3-mercaptopropyltrimethoxysilane, and thiobenzoic acid.

Examples of the sulfinic acid and salts thereof include benzenesulfinic acid, sodium benzenesulfinate, potassium benzenesulfinate, calcium benzenesulfinate, lithium benzenesulfinate, p-toluenesulfinic acid, sodium p-toluenesulfinate, potassium p-toluenesulfinate, calcium p-toluenesulfinate, lithium p-toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, calcium 2,4,6-triethylbenzenesulfinate, lithium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, calcium 2,4,6-triisopropylbenzenesulfinate, and lithium 2,4,6-triisopropylbenzenesulfinate.

Examples of polymerization accelerators preferred for use with the chemical polymerization initiator include amines, sulfinic acid and salts thereof, copper compounds, and tin compounds.

The amines used as polymerization accelerators with the chemical polymerization initiator can be categorized into aliphatic amines, and aromatic amines having an electron withdrawing group on the aromatic ring.

Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethylmethacrylate, N-methyldiethanolamine dimethacrylate, N-ethyldiethanolamine dimethacrylate, triethanolamine monomethacrylate, triethanolamine dimethacrylate, triethanolaminetrimethacrylate, triethanolamine, trimethylamine, triethylamine, and tributylamine. In view of ease of polymerization and storage stability, preferred are tertiary aliphatic amines, more preferably N-methyldiethanolamine and triethanolamine.

Examples of the aromatic amines having an electron withdrawing group on the aromatic ring include tertiary aromatic amines such as N,N-bis(2-hydroxyethyl)-p-toluidine, ethyl 4-(N,N-dimethylamino)benzoate, methyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate.

In view of the ability to impart desirable curability, the aromatic amine having an electron withdrawing group on the aromatic ring is preferably at least one selected from the group consisting of N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

Examples of sulfinic acid and salts thereof used as polymerization accelerators with the chemical polymerization initiator include those exemplified above as polymerization accelerators for the photopolymerization initiator.

Preferred are sodium benzenesulfinate, sodium p-toluenesulfinate, and sodium 2,4,6-triisopropylbenzenesulfinate.

Examples of copper compounds used as polymerization accelerators with the chemical polymerization initiator include copper acetylacetonate, copper(II) acetate, copper oleate, copper(II) chloride, and copper(II) bromide.

Examples of tin compounds used as polymerization accelerators with the chemical polymerization initiator include di-n-butyltin dimaleate, di-n-octyltin dimaleate, di-n-octyltin dilaurate, and di-n-butyltin dilaurate. Preferred are di-n-octyltin dilaurate and di-n-butyltin dilaurate.

The amount of polymerization accelerator is not particularly limited. However, in view of considerations such as ease of polymerization, the polymerization accelerator is preferably 0.01 parts by mass or more, more preferably 0.1 parts by mass or more, even more preferably 1 part by mass or more, and is preferably 10 parts by mass or less, more preferably 3 parts by mass or less relative to 100 parts by mass of the polymerizable monomer.

The content of the polymer in a dental mill blank of the present invention is preferably 5 mass % or more, more preferably 7 mass % or more, even more preferably 10 mass % or more, and is preferably 30 mass % or less, more preferably 25 mass % or less, even more preferably 20 mass % or less. In this way, the dental mill blank can have improved mechanical strength and more desirable aesthetic quality. The polymer content in the dental mill blank can be determined by subtracting the inorganic filler content (mass %) from the total amount (100 mass %), and, when the dental mill blank is containing other components, by subtracting the content (mass %) of other components from the calculated value.

Other Components

A dental mill blank of the present invention may contain other components, such as a pH adjuster, an ultraviolet absorber, an antioxidant, a colorant, a pigment, an antimicrobial agent, an X-ray contrast agent, a thickener, and a fluorescent agent, in addition to the inorganic filler and the polymer, depending on intended use.

Dental Mill Blank Producing Method

A method of production of a dental mill blank of the present invention is not particularly limited. However, for advantages such as more efficiently obtaining a dental mill blank having the desired properties, it is preferable that a dental mill blank of the present invention be produced by (1) a method that comprises pressing an inorganic filler into an inorganic filler molded body and contacting the inorganic filler molded body and a polymerizable monomer-containing composition with each other, and polymerizing and curing the polymerizable monomer (Method 1), or (2) a method that comprises mixing an inorganic filler and a polymerizable monomer-containing composition into a paste, and polymerizing and curing the polymerizable monomer (Method 2). Method 1 is more preferred. The inorganic filler contains inorganic filler (A) and inorganic filler (B), and the inorganic filler (A) is partly forming an aggregate, as described above.

A dental mill blank of the present invention in which the inorganic filler (A) is partly forming an aggregate can be produced using, for example, an inorganic filler containing an inorganic filler (A) forming an aggregate, an inorganic filler (A) not forming an aggregate, and the inorganic filler (B). Such an inorganic filler can be obtained by mixing an inorganic filler (A) forming an aggregate, an inorganic filler (A) not forming an aggregate, and the inorganic filler (B) after separately preparing these fillers. However, for advantages such as more conveniently obtaining the desired inorganic filler, it is preferable that the inorganic filler be obtained by a method that partially disperses the aggregate-forming inorganic filler (A) in a dispersion treatment to prepare a mixture containing the aggregate-forming inorganic filler (A) and the inorganic filler (A) not forming an aggregate, and that mixes this mixture with the inorganic filler (B), or a method by which a mixture of the aggregate-forming inorganic filler (A) and the inorganic filler (B) is subjected to a dispersion treatment to prepare a mixture containing the inorganic filler (A) forming an aggregate, the inorganic filler (A) not forming an aggregate, and the inorganic filler (B).

The dispersion treatment is not particularly limited, and may be, for example, ultrasonic dispersion. The ultrasonic dispersion may be a process that applies ultrasonic waves to a mixture of the inorganic filler and a solvent. The solvent may be, for example, an alcohol (such as, for example, ethanol, methanol, or isopropanol), an ether, or a ketone (such as, for example, acetone, or methyl ethyl ketone).

The output of the ultrasonic dispersion process is not particularly limited, and may be 50 to 2,000 W, preferably 100 to 1,000 W, even more preferably 300 to 900 W. The frequency of the ultrasonic dispersion process is not particularly limited, and may be 20 kHz or more, preferably 25 to 300 kHz, even more preferably 30 to 100 kHz. The temperature of the ultrasonic dispersion process is not particularly limited, and may be 0 to 100° C.

The duration of the ultrasonic dispersion process is not particularly limited. However, because an excessively long ultrasonic dispersion process may cause problems such as complete dispersion of inorganic filler (A), the ultrasonic dispersion process is performed for preferably at least 1 minute, more preferably at least 5 minutes, even more preferably at least 10 minutes, and for preferably at most 12 hours, more preferably at most 6 hours, even more preferably at most 4 hours, though the duration depends on factors such as the output and frequency.

Pressing

The inorganic filler molded body in Method 1 is prepared by pressing the inorganic filler. The method of pressing the inorganic filler is not particularly limited, and a known method may be used. Specific examples of pressing methods include a method that charges the inorganic filler into a pressure mold (die) of a desired size, and uniaxially applies pressure using an upper punch and a lower punch.

The pressure of uniaxial pressing may be appropriately optimized according to conditions such as the desired size of the inorganic filler molded body to be obtained, and the type and particle size of inorganic filler. Typically, the pressure may be 10 MPa or more. Higher pressures are preferred because an increased pressure makes it easier to obtain the desired dental mill blank, and improves the stability of the inorganic filler molded body of when contacting the inorganic filler molded body and the polymerizable monomer-containing composition with each other. However, the pressure should be typically 200 MPa or less considering factors such as the size of inorganic filler molded body, productivity due to factors such as the equipment, and reduction of cracks and chipping in the inorganic filler molded body caused by, for example, friction against the mold under an excessive load. In view of this, the pressure is preferably 20 MPa or more, more preferably 25 MPa or more, and is preferably 180 MPa or less, more preferably 150 MPa or less. The pressing time may be appropriately set according to the pressure, and may be typically 1 to 120 minutes.

The pressing maybe achieved by employing cold isostatic pressing (CIP). In this case, CIP may be employed by itself or with a method other than CIP, such as with the uniaxial pressing described above. Specifically, the pressing may be achieved by CIP without the uniaxial pressing, or by performing CIP after the uniaxial pressing. As a rule, pressing by CIP enables application of higher pressure than by uniaxial pressing, and the pressure can be evenly exerted three-dimensionally on the inorganic filler molded body. By employing CIP, it is therefore possible to solve the undesirable microscopic voids inside the inorganic filler molded body, and the uneven aggregation of inorganic filler particles. The inorganic filler pressed by CIP can also have improved compression density, and the dental mill blank produced can have a high inorganic filler content. When performing CIP for pressing without uniaxial pressing, the inorganic filler may be charged into an container made of a highly elastic material such as silicone rubber or polyisoprene rubber, and may be subjected to CIP either directly or in a reduced pressure state (including a vacuum state). Likewise, in the case where uniaxial pressing is followed by CIP, the molded body from uniaxial pressing may be subjected to CIP either directly or in a reduced pressure state (including a vacuum state).

It is preferable that CIP be performed under high pressure. CIP may be performed by using, for example, a CIP apparatus capable of applying a pressure of about 1,000 MPa (e.g., a CIP apparatus manufactured by Kobe Steel, Ltd.). Higher pressures are preferred in CIP because an increased pressure makes it easier to obtain the desired dental mill blank, and improves the stability of the inorganic filler molded body of when contacting the inorganic filler molded body and the polymerizable monomer-containing composition with each other, regardless of the presence or absence of uniaxial pressing. However, considering factors such as productivity, and reduction of cracks and chipping in the inorganic filler molded body caused by, for example, friction against the mold under an excessive load, the pressure in CIP is preferably 30 MPa or more, more preferably 50 MPa or more, even more preferably 100 MPa or more, and is preferably 300 MPa or less, more preferably 250 MPa or less, even more preferably 200 MPa or less. In CIP, pressure may be applied for a time period that may be appropriately set according to the pressure. Typically, pressure may be applied for 1 to 60 minutes.

The inorganic filler molded body resulting from the pressing of the inorganic filler may have a monolayer structure or a multilayer structure. The multilayer structure may be, for example, a structure with individually pressed layers of different inorganic fillers (for example, inorganic fillers each containing both inorganic filler (A) and inorganic filler (B) but that differ in composition or other properties), or a structure with individually pressed layers of the same inorganic filler (for example, the same inorganic filler containing both inorganic filler (A) and inorganic filler (B)). In either case, the inorganic filler molded body with such a multilayer structure can be processed into a dental mill blank having layers with different color tones, different levels of transparency, and different properties. A dental mill blank having such a multilayer structure can provide a clinically useful dental prosthesis. For example, an aesthetically superior crown having an enamel color in an upper layer and a dentin color in a lower layer can be produced by machining a dental mill blank having a first layer disposed as a layer of an inorganic filler that has been adjusted to have increased transparency upon polymerization and curing of the polymerizable monomer, and a second layer disposed as a layer of an inorganic filler that has been adjusted to impart a color of dentin upon polymerization and curing of the polymerizable monomer.

The method for preparing the inorganic filler that provides the desired color after polymerization and curing is not particularly limited. For example, a method may be used that mixes and disperses a pigment (e.g., colored particles) in an inorganic filler.

The pigment may be selected from known pigments used for dental compositions. The pigment may be an inorganic pigment or an organic pigment.

Examples of the inorganic pigment include chromates such as chrome yellow, zinc yellow, and barium yellow; ferrocyanides such as iron blue; sulfides such as silver vermilion, cadmium yellow, zinc sulfide, antimony white, and cadmium red; sulfates such as barium sulfate, zinc sulfate, and strontium sulfate; oxides such as zinc white, titanium white, red iron oxide, iron black, yellow ferrous oxide, and chromium oxide; hydroxides such as aluminum hydroxide; silicates such as calcium silicate and ultramarine; and carbon materials such as carbon black and graphite.

Examples of the organic pigment include nitroso pigments such as naphthol green B and naphthol green Y nitro pigments such as naphthol S and lithol fast yellow 2G; insoluble azo pigments such as permanent red 4R, brilliant fast scarlet, Hansa yellow, and benzidine yellow; poorly soluble azo pigments such as lithol red, lake red C, and lake red D; soluble azo pigments such as brilliant carmine 6B, permanent red F5R, pigment scarlet 3B, and bordeaux 10B; phthalocyanine pigments such as phthalocyanine blue, phthalocyanine green, and sky blue; basic dye pigments such as rhodamine lake, malachite green lake, and methyl violet lake; and acidic dye pigments such as peacock blue lake, eosin lake, and quinoline yellow lake.

These pigments may be used alone, or two or more thereof may be used in combination, and may be appropriately selected according to the desired color tone.

Preferred among the foregoing examples are titanium white (e.g., Japanese Pharmacopoeia titanium oxide white), red iron oxide, iron black, and yellow ferrous oxide, which are inorganic pigments that excel in properties such as heat resistance and lightfastness.

The pigment content may be appropriately adjusted according to the desired color tone, and is not particularly limited. It is, however, preferable that the pigment content be 0.01 ppm by mass or more, more preferably 0.1 ppm by mass or more, and 5 mass % or less, more preferably 1 mass % or less, in terms of a proportion in the layer in which the pigment is mixed.

Uniform mixing and dispersing of the pigment in the inorganic filler may be achieved by using a known method of mixing and dispersing a powder, and the method may be a dry method or a wet method. However, for advantages such as more uniformly mixing and dispersing the pigment, it is preferable to use a method that includes mixing the inorganic filler and the pigment in the presence of a solvent, and subsequently removing the solvent (for example, by distillation). The mixing may follow a known method, such as by using a disperser such as a sand mill, a bead mill, an attritor, a colloid mill, a ball mill, an ultrasonic homogenizer, a homomixer, a dissolver, or a homogenizer. The mixing conditions may be appropriately selected according to conditions such as the particle sizes and amounts of the inorganic filler and pigment used; the type and amount of the solvent added; and the type of disperser. The dispersing conditions, including dispersing time, stirrer, and rotational speed, may be appropriately selected according to, for example, the dispersibility of each component. The solvent is preferably water, and/or a solvent that is compatible with water. Examples of the solvent include alcohols (for example, ethanol, methanol, isopropanol), ethers, and ketones (for example, acetone, methyl ethyl ketone).

In order to impart a desired color after polymerization and curing, it is also possible to use a method that uses an inorganic filler that itself has a specific color, such as a color glass, aside from mixing and dispersing the pigment in the inorganic filler. Examples of the inorganic filler that itself has a specific color include commercially available porcelain powders, for example, such as the porcelain powders manufactured by VITA under the trade names VM and VM7, and the porcelain powders manufactured by Kuraray Noritake Dental Inc. under the trade names Noritake Super Porcelain AAA and Cerabien ZR. These may be optionally pulverized to adjust the particle size.

In order to provide the desired transparency after polymerization and curing, it is possible to use, for example, a method that adjusts the refractive index and particle size of the inorganic filler. As is known, the transparency of an inorganic filler-dispersed resin increases as the difference between the refractive index of the inorganic filler and the refractive index of the resin itself decreases, or as the particle size deviates from the visible light wavelength (0.4 to 0.7 $\mu$m). It is accordingly preferable to use, for example, a method in which the inorganic filler to be used as a high transparency layer is an inorganic filler having a refractive index that is as close as possible to the post-polymerization and curing refractive index of the polymerizable monomer-containing composition used for impregnation. It is also possible to use a method that appropriately selects a polymerizable monomer so as to match the refractive index with that of the inorganic filler.

As a way of ensuring desired physical properties after polymerization and curing, it is possible to use, for example, a method whereby an inorganic filler having desirable glossiness is used for a layer corresponding to the enamel layer, and an inorganic filler having desirable mechanical strength is used for an inner layer corresponding to the dentin layer. By combining inorganic fillers in this fashion, a crown prosthesis can be provided that exhibits desirable durability in the mouth, and is highly useful for clinical practice.

An inorganic filler molded body having a multilayer structure can be obtained by using the following pressing method, for example. Specifically, a first inorganic filler is charged into a uniaxial pressing mold (die) fitted with a lower punch, and is pressed after setting an upper punch on the mold. After removing the upper punch, a second inorganic filler is charged onto the pressed aggregate of first inorganic filler, and is pressed with the upper punch reattached to the mold. An inorganic filler molded body having a multilayer structure can be obtained by taking it out of the mold after repeating the foregoing procedure for a number of times that depends on the number of layers needed. The applied pressure in the pressing process may be appropriately set according to conditions such as the type and amount of the inorganic filler used, and may be the same or different for each layer. Alternatively, a first inorganic filler and a second inorganic filler may be pressed together after charging the second inorganic filler onto the first inorganic filler that has been charged into the mold and had its surface leveled without being pressed.

In obtaining an inorganic filler molded body having a multilayer structure, the inorganic fillers may be pressed at once into the molded body in the manner described above, or another inorganic filler may be laminated and pressed on a molded body that has been separately molded. Aside from these methods, an inorganic filler molded body having a multilayer structure also can be obtained by laminating and pressing molded bodies that have been separately molded.

The shape and size of the pressed inorganic filler molded body are not particularly limited, and may be appropriately adjusted according to the shape and size of the dental mill blank described below.

Contact Between Inorganic Filler Molded Body and Polymerizable Monomer-Containing Composition In Method 1, the polymerizable monomer-containing composition penetrates into spaces between particles in the inorganic filler molded body upon being brought into contact with the inorganic filler molded body. This produces a composition in which the inorganic filler particles are very densely dispersed in the polymerizable monomer-containing composition. In view of this, it is preferable in Method 1 to use an inorganic filler molded body that is not formed into a porous body by sintering and communicating.

As a Rule, a Particle-Dispersed Composite Material can Produce a Crown restoration material that can be desirably polished to gloss, and that can remain glossy in the mouth for prolonged time periods as the particle size of the inorganic filler dispersed in the resin becomes smaller. However, high-density packing of inorganic filler in the composite material becomes difficult to achieve, and the mechanical strength and the resistance of the cured product against wear in opposing teeth tend to decrease as the particle size of inorganic filler becomes smaller. Method 1 produces a dental mill blank by pressing the inorganic filler into an inorganic filler molded body and contacting the inorganic filler molded body and a polymerizable monomer-containing composition with each other, and polymerizing and curing the polymerizable monomer. In this way, the inorganic filler can be packed in high density, and the dental mill blank can produce a dental prosthesis having desirable gloss and improved strength and improved resistance against wear in opposing teeth.

The method for contacting the inorganic filler molded body and the polymerizable monomer-containing composition with each other is not particularly limited, and this may be achieved by a method that allows the polymerizable monomer-containing composition to penetrate into spaces between inorganic filler particles. Preferred for advantages such as convenience is a method that immerses the inorganic filler molded body in the polymerizable monomer-containing composition. In this way, the polymerizable monomer-containing composition is able to gradually permeate into the inorganic filler molded body by capillary action. Here, it is preferable that the inorganic filler molded body be immersed in a reduced pressure atmosphere environment because it promotes permeation of the polymerizable monomer-containing liquid composition. By switching pressure between reduced pressure and ordinary pressure in a repeated cycle (a reduced pressure/ordinary pressure cycle), it is possible to promote further penetration of the polymerizable monomer-containing composition, and reduce the time for the polymerizable monomer-containing composition to fully permeate the inorganic filler molded body. The pressure in the reduced pressure atmosphere may be appropriately adjusted according to conditions such as the viscosity of the polymerizable monomer-containing composition, and the particle size of the inorganic filler. However, the pressure is preferably 10 kPa or less, more preferably 5 kPa or less, even more preferably 2 kPa or less, and is preferably 0.1 Pa or more, more preferably 1 Pa or more, even more preferably 10 Pa or more. The reduced pressure atmosphere may be a vacuum (for example, about $1\times10^{-8}$ to $1\times10^{-1}$ Pa).

Aside from immersing the inorganic filler molded body in the polymerizable monomer-containing composition, the polymerizable monomer-containing composition may be fed to the inorganic filler molded body in a mold under applied pressure upon pressing the inorganic filler in the mold. In this way, the polymerization and curing of the polymerizable monomer can be directly carried out in the mold following this procedure. The pressure applied to feed the polymerizable monomer-containing composition to the inorganic filler molded body is preferably 2 MPa or more, more preferably 10 MPa or more, even more preferably 20 MPa or more.

An inorganic filler molded body that has been apparently impregnated with the polymerizable monomer-containing composition after being brought into contact with the polymerizable monomer-containing composition such as by immersion may be placed under increased pressure conditions for a certain time period so that the polymerizable monomer-containing composition can more efficiently permeate into the inorganic filler molded body without leaving spaces in the inorganic filler molded body. The increased pressure can be created by using, for example, a CIP apparatus. The pressure is preferably 20 MPa or more, more preferably 50 MPa or more, even more preferably 100 MPa or more. Pressure may be repeatedly switched between increased pressure and ordinary pressure in a cycle (an increased pressure/ordinary pressure cycle).

For advantages such as more efficient permeation of the polymerizable monomer-containing composition into the inorganic filler molded body, the inorganic filler molded body and the polymerizable monomer-containing composition are contacted with each other at a temperature of preferably 0° C. or more, more preferably 10° C. or more, even more preferably 20° C. or more. The temperature may be 30° C. or more, 40° C. or more, or 50° C. or more. The temperature is preferably 70° C. or less, more preferably 60° C. or less.

The contact time of the inorganic filler molded body and the polymerizable monomer-containing composition depends on factors such as the type of inorganic filler, the size of inorganic filler molded body, the extent of permeation of the polymerizable monomer, and the contact method, and may be appropriately adjusted. For example, in the case where the inorganic filler molded body is immersed in the polymerizable monomer-containing composition, the contact time maybe typically 0.1 to 240 hours. The contact time maybe 0.5 to 120 hours when the contact is made in a reduced pressure atmosphere. The contact time may be 0.2 to 48 hours when the polymerizable monomer-containing composition is fed to the inorganic filler molded body under an applied pressure to the inorganic filler molded body.

Polymerizable Monomer-Containing Composition

The content of the polymerizable monomer in the polymerizable monomer-containing composition used in Methods 1 and 2 may be, for example, 50 mass % or more, and is preferably 80 mass % or more, more preferably 90 mass % or more, even more preferably 95 mass % or more, particularly preferably 98 mass % or more.

Preferably, the polymerizable monomer-containing composition additionally contains the polymerization initiator, and more preferably contains the polymerization initiator and the polymerization accelerator. The polymerization initiator and the polymerization accelerator in the polymerizable monomer-containing composition may be used in the contents specified above for the polymerization initiator and the polymerization accelerator. When producing a dental mill blank containing these other components, the additional components may be incorporated in the polymerizable monomer-containing composition.

The method for preparing the polymerizable monomer-containing composition is not particularly limited. For example, the polymerizable monomer-containing composition may be prepared by mixing the polymerization initiator, the polymerization accelerator, and any other components into a polymerizable monomer.

As a rule, the polymerizable monomer-containing composition permeates into the inorganic filler molded body at a rate that increases with decrease of viscosity. Preferably, the viscosity (25° C.) of the polymerizable monomer-containing composition is 10 Pa·s or less, more preferably 5 Pa·s or less, even more preferably 2 Pa·s or less. The viscosity may be adjusted by, for example, appropriately selecting a polymerizable monomer. Aside from the purpose to adjust the viscosity of the polymerizable monomer-containing composition, it is preferable that the polymerizable monomer contained in the polymerizable monomer-containing composition be selected by also taking into account the mechanical strength and the refractive index of the dental mill blank to be produced. The viscosity of the polymerizable monomer-containing composition also can be lowered by, for example, containing a solvent. In this case, the solvent may be removed in the subsequent process of reducing pressure. The permeation rate can be increased by increasing temperature and lowering the viscosity of the polymerizable monomer-containing composition. The increased temperature range may be the same temperature range specified above for the contact temperature of the inorganic filler molded body and the polymerizable monomer-containing composition.

Preparation of Paste

In Method 2, the method used to prepare a paste by mixing the inorganic filler and the polymerizable monomer-containing composition is not particularly limited, and this may be achieved by, for example, kneading the inorganic filler and the polymerizable monomer-containing composition. Optionally, the method may involve vacuum degassing of the paste during or after the mixing process.

Polymerization and Curing of Polymerizable Monomer

In Method 1, the desired dental mill blank can be obtained by polymerizing and curing the polymerizable monomer contained in the polymerizable monomer-containing composition having penetrated into the inorganic filler molded body as a result of being brought into contact with the inorganic filler molded body (a state where the inorganic filler molded body is impregnated with the polymerizable monomer-containing composition). In Method 2, the desired dental mill blank can be obtained by polymerizing and curing the polymerizable monomer contained in the paste. For advantages such as more easily obtaining a dental mill blank of the desired shape, it is preferable in the case of the latter that the polymerization and curing be performed after the paste is molded in a mold. The molding of the paste may optionally involve pressing.

The method of polymerization and curing is not particularly limited, and may be appropriately selected from polymerization methods such as thermal polymerization, photo-polymerization, and chemical polymerization, according to factors such as the type of the polymerization initiator used. In the case of thermal polymerization, the heating temperature is not particularly limited, and may be, for example, 40 to 150° C. The heating time is not particularly limited either, and may be, for example, 1 to 70 hours. The thermal polymerization may be carried out in one step or in multiple steps. In the case of the latter, the heating temperature may be appropriately varied. In the case of photo-polymerization, the light used is not limited to a particular type of light, and may be visible light, ultraviolet light, or any other light. The photo-polymerization time is not particularly limited either, and may be, for example, 1 to 20 minutes. In view of increasing the polymerization conversion rate to obtain a dental mill blank having even higher mechanical strength, photo-polymerization may be followed by thermal polymerization.

The polymerization conversion rate can improve, and the dental mill blank produced can have even higher mechanical strength when the inorganic filler molded body impregnated with the polymerizable monomer-containing composition, or the paste prepared by mixing the inorganic filler and the polymerizable monomer-containing composition is subjected to polymerization and curing in an inert gas atmosphere such as a nitrogen gas atmosphere, or under reduced pressure (including vacuum conditions). In the case where polymerization and curing is carried out under reduced pressure (including vacuum conditions), it is preferable in view of advantages such as productivity that the inorganic filler molded body impregnated with the polymerizable monomer-containing composition, or the paste prepared by mixing the inorganic filler and the polymerizable monomer-containing composition be subjected to polymerization and curing by being packed in a vacuum pack or the like. In this case, polymerization and curing may employ thermal polymerization under applied pressure, using, for example, an autoclave.

For advantages such as further improving the mechanical strength of the dental mill blank produced, the inorganic filler molded body impregnated with the polymerizable monomer-containing composition, or the paste prepared by mixing the inorganic filler and the polymerizable monomer-containing composition may be subjected to polymerization and curing under applied pressure. By being placed under applied pressure, the inorganic filler molded body impregnated with the polymerizable monomer-containing composition, or the paste prepared by mixing the inorganic filler and the polymerizable monomer-containing composition enables the polymerizable monomer-containing composition to more effectively enter the fine spaces between the inorganic filler particles, and the number of remaining fine bubbles can be reduced. By being placed under applied pressure, the inorganic filler and the polymerizable monomer also can be brought closer together, and the mechanical strength of the dental mill blank can further improve as a result of an increased interaction between the inorganic filler and the polymerizable monomer.

In the case where polymerization and curing is carried out under applied pressure, the pressure is preferably 20 MPa or more, more preferably 50 MPa or more, even more preferably 100 MPa or more, particularly preferably 200 MPa or more. It is preferable to apply as high a pressure as possible, and the pressure may be appropriately set taking into account, for example, the capacity of the pressure device actually used. Examples of the pressure device include an autoclave, a CIP apparatus, and a HIP (hot isostatic pressing) apparatus. For example, a CIP apparatus capable of applying a pressure of about 1,000 MPa (e.g., a CIP apparatus manufactured by Kobe Steel, Ltd.) may be used. When carried out under applied pressure, the polymerization and curing may employ thermal polymerization, which applies heat for polymerization and curing, or may employ photopolymerization or chemical polymerization.

As a specific preferred example, the polymerization under applied pressure may be carried out by placing and sealing the inorganic filler molded body impregnated with the polymerizable monomer-containing composition, or the paste prepared by mixing the inorganic filler and the polymerizable monomer-containing composition in a vacuum pack, and polymerizing the monomer under applied pressure, using, for example, a CIP apparatus. In this way, the dental mill blank produced can have even higher mechanical strength. In the case where polymerization is carried out under applied pressure using a CIP apparatus, the processing chamber of the CIP apparatus may be heated after applying a predetermined pressure. Specifically, for example, a predetermined pressure is applied at room temperature to the inorganic filler molded body impregnated with the polymerizable monomer-containing composition, or to the paste prepared by mixing the inorganic filler and the polymerizable monomer-containing composition, inside the processing chamber of a CIP apparatus, and the chamber is heated over a time period of from about 30 minutes to about 24 hours until it reaches a predetermined target temperature. The target temperature may be, for example, 80 to 180° C. The polymerization time and the target temperature may be set taking into account factors such as the decomposition temperature of the polymerization initiator used.

The dental mill blank produced in Method 2 may have a monolayer structure or a multilayer structure, as with the case of Method 1. The multilayer structure may be, for example, a structure having layers derived from pastes containing different inorganic fillers, or a structure having layers derived from pastes containing the same inorganic filler. In either case, a dental mill blank having layers with different color tones, different levels of transparency, and different properties can be provided, and a dental mill blank having such a multilayer structure can provide a clinically useful dental prosthesis, as with the case of Method 1. For example, an aesthetically superior crown having an enamel color in an upper layer and a dentin color in a lower layer can be produced by machining a dental mill blank having a first layer disposed as a layer formed by a paste that has been adjusted to have increased transparency upon polymerization and curing of the polymerizable monomer, and a second layer disposed as a layer formed by a paste that has been adjusted to impart a color of dentin upon polymerization and curing of the polymerizable monomer.

The method used to prepare the paste that can impart the desired color after polymerization and curing is not particularly limited, and may be, for example, a method that mixes a pigment (color particles) into the paste. The pigment may be, for example, the same pigment mentioned above in conjunction with the inorganic filler molded body having a multilayer structure. The method for imparting the desired color after polymerization and curing may be, for example, a method that uses an inorganic filler that itself has a specific color, such as the color glass mentioned above.

When using Method 2, a dental mill blank having a multilayer structure can be produced in the manner described below, for example. Specifically, a first paste is charged into a uniaxial pressing mold (die) fitted with a lower punch, and is pressed after setting an upper punch on the mold. The first paste is then polymerized and cured to form a first layer. After removing the upper punch, a second paste is charged onto the first layer, and is pressed with the upper punch reattached to the mold. The second paste is then polymerized and cured to form a second layer. A dental mill blank having a multilayer structure can then be obtained by taking the cured product out of the mold after repeating the foregoing procedure for a number of times that depends on the number of layers needed. The applied pressure in the pressing process may be appropriately set according to conditions such as the type and amount of the paste used, and may be the same or different for each layer. Alternatively, for polymerization and curing, a first paste and a second paste may be pressed together after charging the second paste onto the first paste that has been charged into the mold and had its surface leveled without being pressed.

The cured product obtained after the foregoing polymerization and curing process may be used directly as a dental mill blank. However, by performing a heat treatment after polymerization and curing, the stress-induced strain that generates in the cured product can be relaxed, and damage that may occur while machining the dental mill blank into a dental prosthesis or during clinical use of the dental prosthesis can be reduced. The heat treatment temperature may be, for example, 80 to 150° C. The heat treatment may be performed for, for example, 10 to 120 minutes.

The cured product from the foregoing polymerization and curing process may be prepared into a dental mill blank by being optionally cut and milled into the desired size, and polishing the surface.

Dental Mill Blank

A dental mill blank of the present invention has use in dentistry, and may be used for, for example, fabrication of dental prostheses through processes such as cutting, carving, and milling. With the dental mill blank, a dental prosthesis that exhibits desirable resistance against wear in opposing teeth can be obtained.

Examples of such dental prostheses include crown restorations such as inlays, onlays, veneers, crowns, and bridges; abutment teeth, dental posts, dentures, denture bases, and implant parts (e.g., fixtures, abutments). Preferably, the dental mill blank is processed with a dental CAD/CAM system. Examples of the dental CAD/CAM system include the CEREC system manufactured by Sirona Dental Systems Inc., and the Katana system manufactured by Kuraray Noritake Dental Inc.

The shape of a dental mill blank of the present invention is not particularly limited, and may be appropriately set according to considerations such as intended use. For example, a dental mill blank of the present invention may have a prism shape such as a triangular prism, a quadrangular prism, or a hexagonal prism; or a cylindrical shape such as a disc (disc-like) shape.

The size of a dental mill blank of the present invention is not particularly limited, and may be, for example, a size that can be set in a commercially available dental CAD/CAM system. Specific examples of the size of a dental mill blank of the present invention include a 40 mm×20 mm×15 mm prism suited for fabrication of, for example, single bridges, a 17 mm×10 mm×10 mm prism suited for fabrication of, for example, inlays and onlays, a 14 mm×18 mm×20 mm prism suited for fabrication of, for example, full crowns, and a disc having a diameter of 100 mm and a thickness of 10 to 28 mm suited for fabrication of, for example, long-span bridges and denture bases.

EXAMPLES

The following specifically describes the present invention by way of Examples and Comparative Examples. It should be noted that the present invention is in no way limited by the following Examples. Details of the components used are as follows.

Inorganic Filler
UF2.0: Barium glass (average primary particle diameter 2.0 μm, manufactured by Schott)
UF1.0: Barium glass (average primary particle diameter 1.0 μm, manufactured by Schott)
UF0.4: Barium glass (average primary particle diameter 0.4 μm, manufactured by Schott)
NF180: Barium glass (average primary particle diameter 0.18 μm, manufactured by Schott)
Ox-50: Fine silica particles (average primary particle diameter 0.04 μm, manufactured by Nippon Aerosil Co., Ltd.)
Surface Treatment Agent
γ-MPS: γ-Methacryloyloxypropyltrimethoxysilane (manufactured by Shin-Etsu Chemical Co., Ltd.)
Binder
UDMA: [2,2,4-Trimethylhexamethylenebis(2-carbamoyloxyethyl)]dimethacrylate
Polymerizable Monomer
UDMA: [2,2,4-Trimethylhexamethylenebis(2-carbamoyloxyethyl)]dimethacrylate
3G: Triethylene glycol dimethacrylate
Polymerization Initiator
THP: 1,1,3,3-Tetramethylbutylhydroperoxide (manufactured by NOF Corporation)

Production Example 1

Production of Inorganic Filler (F1)
For production of inorganic filler (F1), 100 parts by mass of a mixture of 70 parts by mass of UF2.0 and 30 parts by mass of NF180 was dispersed in 300 parts by mass of ethanol, and the resulting mixture was ultrasonically dispersed at 720 W output and 40 kHz frequency for 30 minutes using an ultrasonic oscillator. The mixture was then stirred at room temperature for 2 hours after adding 2.5 parts by mass of γ-MPS, 0.15 parts by mass of acetic acid, and 5 parts by mass of water. The solvent was distilled away under reduced pressure, and an inorganic filler (F1) was obtained after a surface treatment carried out by drying at 90° C. for 3 hours with a surface treatment agent.

Production Example 2

Production of Inorganic Filler (F2)
For production of inorganic filler (F2), 100 parts by mass of a mixture of 70 parts by mass of UF2.0 and 30 parts by mass of NF180 was dispersed in 300 parts by mass of ethanol, and the resulting mixture was ultrasonically dispersed at 730 W output and 28 kHz frequency for 30 minutes using an ultrasonic oscillator. The mixture was then stirred at room temperature for 2 hours after adding 2.5 parts by mass of γ-MPS, 0.15 parts by mass of acetic acid, and 5 parts by mass of water. The solvent was distilled away under reduced pressure, and an inorganic filler (F2) was obtained after a surface treatment carried out by drying at 90° C. for 3 hours with a surface treatment agent.

Production Example 3

Production of Inorganic Filler (F3)
For production of inorganic filler (F3), 100 parts by mass of a mixture of 70 parts by mass of UF2.0 and 30 parts by mass of NF180 was dispersed in 300 parts by mass of ethanol, and the resulting mixture was ultrasonically dispersed at 720 W output and 40 kHz frequency for 180 minutes using an ultrasonic oscillator. The mixture was then stirred at room temperature for 2 hours after adding 2.5 parts by mass of 7-MPS, 0.15 parts by mass of acetic acid, and 5 parts by mass of water. The solvent was distilled away under reduced pressure, and an inorganic filler (F3) was obtained after a surface treatment carried out by drying at 90° C. for 3 hours with a surface treatment agent.

Production Example 4

Production of Inorganic Filler (F4)
For production of inorganic filler (F4), 100 parts by mass of a mixture of 70 parts by mass of UF1.0 and 30 parts by mass of NF180 was dispersed in 300 parts by mass of ethanol, and the resulting mixture was ultrasonically dispersed at 720 W output and 40 kHz frequency for 30 minutes using an ultrasonic oscillator. The mixture was then stirred at room temperature for 2 hours after adding 5 parts by mass of 7-MPS, 0.15 parts by mass of acetic acid, and 5 parts by mass of water. The solvent was distilled away under reduced pressure, and an inorganic filler (F4) was obtained after a surface treatment carried out by drying at 90° C. for 3 hours with a surface treatment agent.

Production Example 5

Production of Inorganic Filler (F5)
For production of inorganic filler (F5), 100 parts by mass of a mixture of 80 parts by mass of UF0.4 and 20 parts by mass of Ox-50 was dispersed in 300 parts by mass of ethanol, and the resulting mixture was ultrasonically dispersed at 720 W output and 40 kHz frequency for 60 minutes using an ultrasonic oscillator. The mixture was then stirred at room temperature for 2 hours after adding 11 parts by mass of γ-MPS, 0.15 parts by mass of acetic acid, and 5 parts by mass of water. The solvent was distilled away under reduced pressure, and an inorganic filler (F5) was obtained after a surface treatment carried out by drying at 90° C. for 3 hours with a surface treatment agent.

Production Example 6

Production of Inorganic Filler (F6)
For production of inorganic filler (F6), 30 parts by mass of NF180 was dispersed in 300 parts by mass of ethanol, and the resulting mixture was ultrasonically dispersed at 720 W output and 40 kHz frequency for 24 hours using an ultrasonic oscillator. After adding 70 parts by mass of UF2.0, the mixture was ultrasonically dispersed at 720 W output and 40 kHz frequency for 30 minutes. The mixture was then stirred at room temperature for 2 hours after adding 2.5 parts by mass of γ-MPS, 0.15 parts by mass of acetic acid, and 5 parts by mass of water. The solvent was distilled away under reduced pressure, and an inorganic filler (F6) was obtained after a surface treatment carried out by drying at 90° C. for 3 hours with a surface treatment agent.

Production Example 7

Production of Inorganic Filler (F7)

For production of inorganic filler (F7), 100 parts by mass of a mixture of 70 parts by mass of UF2.0 and 30 parts by mass of NF180 was dispersed in 300 parts by mass of ethanol, and the resulting mixture was stirred at room temperature for 2 hours after adding 2.5 parts by mass of γ-MPS, 0.15 parts by mass of acetic acid, and 5 parts by mass of water, without ultrasonic dispersion. The solvent was distilled away under reduced pressure, and an inorganic filler (F7) was obtained after a surface treatment carried out by drying at 90° C. for 3 hours with a surface treatment agent.

Production Example 8

Production of Inorganic Filler (F8)

For production of inorganic filler (F8), 100 parts by mass of a mixture of 70 parts by mass of UF2.0 and 30 parts by mass of UF0.4 was dispersed in 300 parts by mass of ethanol, and the resulting mixture was ultrasonically dispersed at 720 W output and 40 kHz frequency for 30 minutes using an ultrasonic oscillator. The mixture was then stirred at room temperature for 2 hours after adding 2.5 parts by mass of γ-MPS, 0.15 parts by mass of acetic acid, and 5 parts by mass of water. The solvent was distilled away under reduced pressure, and an inorganic filler (F8) was obtained after a surface treatment carried out by drying at 90° C. for 3 hours with a surface treatment agent.

Production Example 9

Production of Polymerizable Monomer-Containing Composition (P1)

For preparation of a polymerizable monomer-containing composition (P1), 1 part by mass of THP was dissolved as polymerization initiator in 99 parts by mass of UDMA.

Production Example 10

Production of Polymerizable Monomer-Containing Composition (P2)

For preparation of a polymerizable monomer-containing composition (P2), 1 part by mass of THP was dissolved as polymerization initiator in 80 parts by mass of UDMA and 19 parts by mass of 3G.

Example 1

(1) In Example 1, 7.0 g of the inorganic filler (F1) obtained in Production Example was laid on a lower punching rod of a pressure mold having a 14.5 mm×18 mm rectangular hole. After leveling the powder by tapping, an upper punching rod was set above, and a pressure of 10 kN (38.3 MPa) was uniaxially applied for 2 minutes using a desktop pressing machine. The resulting molded body as an aggregate of inorganic filler (F1) was taken out of the mold by removing the upper and lower punching rods, and was pressed under a pressure of 170 MPa for 5 minutes by CIP to obtain an inorganic filler molded body.

(2) The inorganic filler molded body was immersed in polymerizable monomer-containing composition (P1). After removing air under reduced pressure (10 hPa), the whole was allowed to stand at 70° C. for 48 hours to obtain an inorganic filler molded body impregnated with the polymerizable monomer-containing composition (polymerizable monomer impregnated molded body). The polymerizable monomer impregnated molded body was heated at 110° C. for 7 hours, and at 150° C. for 7 hours with a hot-air dryer to obtain the desired dental mill blank, rectangular in shape.

Examples 2 to 6, and Comparative Examples 1 to 3

Rectangular dental mill blanks were obtained in the same manner as in Example 1, except that the inorganic fillers and the polymerizable monomer-containing compositions shown in Table 1 were used.

In Example 6, the inorganic filler molded body in step (2) was immersed in polymerizable monomer-containing composition (P2), and, after removing air under reduced pressure (10 hPa), the whole was allowed to stand at 40° C. for 48 hours to obtain a polymerizable monomer impregnated molded body. The polymerizable monomer impregnated molded body was heated at 55° C. for 18 hours, and at 110° C. for 3 hours with a hot-air dryer to obtain the desired dental mill blank, rectangular in shape.

Example 7

A paste was prepared by uniformly mixing and kneading 75 g of the inorganic filler (F1) and 25 g of the polymerizable monomer-containing composition (P2) obtained in the Production Example, and degassing the uniform mixture in a vacuum. The mixture was poured into a rectangular mold (14.5 mm×14.5 mm×18 mm), and oxygen was removed by vacuum degassing. After releasing the reduced pressure, the molded body was pressed at 50 MPa, and the resulting molded body was heated at 55° C. for 18 hours, and at 110° C. for 3 hours to obtain the desired dental mill blank, rectangular in shape.

Test Example 1

Cross Section Microscopy

By microscopy, a cross section of the dental mill blank was observed for the presence of an island component formed by the aggregate, and a sea component containing inorganic filler (A) and inorganic filler (B). The observed image was then used for the measurement and calculation of (i) the average particle diameter (x) of island component (aggregate), (ii) the area fraction of island component (aggregate), (iii) the ratio [total area of inorganic filler (A) and inorganic filler (B)]/[polymer area] in the sea component, and (iv) the ratio [area of inorganic filler (A)]/[polymer area] in the island component.

Specifically, a specimen (10 mm×10 mm×1.2 mm) was taken from the dental mill blank using a diamond cutter, and a clean, smooth surface of the specimen was polished under dry conditions, using a #1000 abrasive paper, a #2000 abrasive paper, a #3000 abrasive paper, and a lapping film, in this order. The polished surface was then imaged with a scanning electron microscope (SEM; SU3500 manufactured by HITACHI HIGH-TECHNOLOGIES CORPORATION) at 300 times magnification.

(i) Average Particle Diameter (x) of Island Component (Aggregate)

The particle diameter was measured for all the island components (aggregates; at least 200 particles) observed in a unit field of the SEM image, using image-analyzing particle-size-distribution measurement software (Macview, manufactured by Mountech Co., Ltd.). Here, the particle diameter of an island component (aggregate) was measured as the diameter of a corresponding circle having the same area as the island component (aggregate). The measured particle diameters of the island components (aggregates) were averaged to find the average particle diameter (x) of the island components (aggregates).

(ii) Area Fraction of Island Component (Aggregate)

The total area of the island components (aggregates) was determined from the SEM image using image-analyzing particle-size-distribution measurement software (Macview, manufactured by Mountech Co., Ltd.), and the area fraction of island components was determined by dividing the measured value by the whole area. Particles with a diameter of less than 5 m were not regarded as island components.

(iii) [Total Area of Inorganic Filler (A) and Inorganic Filler (B)]/[Polymer Area] in Sea Component The total area of inorganic filler (A), the total area of inorganic filler (B), and the total area of the polymer in the sea component were determined from the SEM image using image-analyzing particle-size-distribution measurement software (Macview, manufactured by Mountech Co., Ltd.), and the area ratio was determined by dividing the sum of the total areas of inorganic filler (A) and inorganic filler (B) by the total area of the polymer.

(iv) [Area of Inorganic Filler (A)]/[Polymer Area] in Island Component

The total area of inorganic filler (A) and the total area of the polymer in the island component were determined from the SEM image using image-analyzing particle-size-distribution measurement software (Macview, manufactured by Mountech Co., Ltd.), and the area ratio was determined by dividing the total area of inorganic filler (A) by the total area of the polymer. Particles with a diameter of less than 5 μm were not regarded as island components.

Test Example 2

Abrasiveness Test

The dental mill blank was measured for its abrasiveness to opposing teeth, as follows. Specifically, the dental mill blank was ground into a hemispherical sample (0=10.0 mm) with a dental milling machine DWX-50 (manufactured by Roland DG Corporation), and the surface was polished with a laboratory micromotor using carborundum, a silicone point (brown), a silicone point (blue), a brush (a polishing agent for Esutenia), and a felt (diamond paste 1 μm), in this order. Separately, the enamel of a bovine tooth was polished with a #1000 abrasive paper to expose a flat surface. With these samples set on an abrasion tester (manufactured by Navik Corporation), the hemispherical sample was brought into contact with the bovine tooth secured to the tester, and was rotated 35 under an applied load against the bovine enamel in water at room temperature while maintaining contact (initial state). Here, the applied load is 15.6 kg/cm$^2$, and the operational duration is 1 second. After 1 second, the sample was brought back to the initial state by releasing the load and rerotating the sample by −35°. This cycle was repeated 100,000 times. The width and depth of a wear mark on bovine enamel was then measured to determine an amount of wear (wear volume) relative to a flat surface portion of bovine enamel that did not contact the sample (wear depth 0 μm), using a surface roughness meter (a laser confocal displacement meter LT-8100 manufactured by Keyence). The measured value was used as an index of the abrasiveness of the dental mill blank to opposing teeth. The amount of wear on bovine enamel was measured three times per sample, and measured values from two samples were averaged. The results are presented in Table 1. The amount of wear is preferably 0.12 mm$^3$ or less, more preferably 0.1 mm$^3$ or less, even more preferably 0.08 mm$^3$ or less, particularly preferably 0.06 mm$^3$ or less, most preferably 0.05 mm$^3$ or less. The amount of wear maybe, for example, 0.01 mm$^3$ or more.

TABLE 1

| | | | Example | | | | | | | Comparative Example | | |
|---|---|---|---|---|---|---|---|---|---|---|---|---|
| | | | 1 | 2 | 3 | 4 | 5 | 6 | 7 | 1 | 2 | 3 |
| Inorganic filler | | | | | | | | | | | | |
| | Type | | (F1) | (F2) | (F3) | (F4) | (F5) | (F1) | (F1) | (F6) | (F7) | (F8) |
| UF2.0 | (Average primary particle diameter: 2.0 μm) | parts by mass | 70 | 70 | 70 | | | 70 | 70 | 70 | 70 | 70 |
| UF1.0 | (Average primary particle diameter: 1.0 μm) | parts by mass | | | | | 70 | | | | | |
| UF0.4 | (Average primary particle diameter: 0.4 μm) | parts by mass | | | | | | 80 | | | | 30 |
| NF180 | (Average primary particle diameter: 0.18 μm) | parts by mass | 30 | 30 | 30 | 30 | | 30 | 30 | 30 | 30 | |
| Ox-50 | (Average primary particle diameter: 0.04 μm) | parts by mass | | | | | 20 | | | | | |
| Polmerizable monomer-containing composition | | | | | | | | | | | | |
| | Type | | (P1) | (P1) | (P1) | (P1) | (P1) | (P2) | (P2) | (P1) | (P1) | (P1) |
| Dental mill blank | | | | | | | | | | | | |
| Average particle diameter of aggregate (x) | | μm | 32 | 73 | 17 | 38 | 26 | 31 | 29 | 3 | 98 | —*1) |
| Area ratio of island component | | area % | 12 | 18 | 6 | 14 | 13 | 12 | 11 | —*1) | 24 | —*1) |
| Area ratio of polymer in sea component *2) | | area/area | 69/31 | 64/36 | 71/29 | 61/39 | 76/24 | 69/31 | 61/39 | 81/19 | 57/43 | 52/48 |

TABLE 1-continued

|  |  | Example | | | | | | | Comparative Example | | |
| --- | --- | --- | --- | --- | --- | --- | --- | --- | --- | --- | --- |
|  |  | 1 | 2 | 3 | 4 | 5 | 6 | 7 | 1 | 2 | 3 |
| Area ratio of polymer in island component *3) | area/area | 54/46 | 51/49 | 55/45 | 52/48 | 51/49 | 54/46 | 54/46 | —*1) | 42/58 | —*1) |
| Amount of wear | mm$^3$ | 0.042 | 0.039 | 0.055 | 0.049 | 0.033 | 0.049 | 0.053 | 0.192 | 0.144 | 0.231 |

*1) No observable island component
*2) [Total area of inorganic filler (A) and inorganic filler (B)]/[polymer area] in sea component
*3) [Area of inorganic filler (A)]/[polymer area] in island component The dental mill blanks of Examples 1 to 7 all produced small amounts of wear, and exhibited desirable resistance against wear in opposing teeth. The dental mill blanks of Comparative Examples 1 to 3 were inferior to the dental mill blanks of Examples in terms of abrasiveness to opposing teeth.

The invention claimed is:

1. A dental mill blank comprising:
   an inorganic filler containing an inorganic filler (A) and an inorganic filler (B); and
   a polymer,
   the inorganic filler (A) partly forming an aggregate, and the dental mill blank satisfying the following formulae (I) to (III), $$0.001 \leq a < 0.3 \quad (I)$$

$$0.3 \leq b \leq 10 \quad (II)$$

$$10 \leq x \leq 80 \quad (III),$$

where a is an average primary particle diameter of the inorganic filler (A) in micrometers, b is an average primary particle diameter of the inorganic filler (B) in micrometers, and x is an average particle diameter of the aggregate in micrometers.

2. The dental mill blank according to claim 1, comprising an island component containing the aggregate, and a sea component containing the inorganic filler (A) and the inorganic filler (B).

3. The dental mill blank according to claim 2, wherein the island component has an area fraction of 5 to 20% in a cross section observed with a microscope.

4. The dental mill blank according to claim 2, wherein the sea component has a ratio of [total area of inorganic filler (A) and inorganic filler (B)]/[polymer area] of 60/40 to 80/20 as measured in a cross section observed with a microscope.

5. The dental mill blank according to claim 2, wherein the island component has a ratio of [area of inorganic filler (A)]/[polymer area] of 50/50 to 60/40 as measured in a cross section observed with a microscope.

6. The dental mill blank according to claim 1, wherein the content of the inorganic filler is 70 to 95 mass %.

7. The dental mill blank according to claim 1, wherein the content of the polymer is 5 to 30 mass %.

8. The dental mill blank according to claim 1, wherein the dental mill blank has a mass ratio of [content of inorganic filler (A)]/[content of inorganic filler (B)] of 10/90 to 40/60.

9. The dental mill blank according to claim 1, wherein the content of the aggregate is 2 to 15 mass %.

10. A method for producing the dental mill blank of claim 1, comprising pressing an inorganic filler into an inorganic filler molded body and contacting the inorganic filler molded body and a polymerizable monomer-containing composition with each other, and polymerizing and curing the polymerizable monomer.

11. The method according to claim 10, wherein the pressing comprises cold isostatic pressing (CIP).

12. A method for producing the dental mill blank of claim 1, comprising mixing an inorganic filler and a polymerizable monomer-containing composition into a paste, and polymerizing and curing the polymerizable monomer.

* * * * *